(12) United States Patent
Richter et al.

(10) Patent No.: US 10,871,490 B2
(45) Date of Patent: Dec. 22, 2020

(54) ASSAY FOR DETECTION OF CHIMERIC ANTIGEN RECEPTOR T CELLS

(71) Applicant: Miltenyi Biotec GmbH, Bergisch Gladbach (DE)

(72) Inventors: Anne Richter, Cologne (DE); Michaela Niemoller, Bergisch Gladbach (DE); Volker Nolle, Kurten (DE); Stefan Miltenyi, Bergisch Gladbach (DE); Mario Assenmacher, Bergisch Gladbach (DE)

(73) Assignee: Multenyi Biotec, gmbH, Bergisch Gladbach (DE)

( * ) Notice: Subject to any disclaimer, the term of this patent is extended or adjusted under 35 U.S.C. 154(b) by 395 days.

(21) Appl. No.: 15/417,292

(22) Filed: Jan. 27, 2017

(65) Prior Publication Data

US 2017/0248594 A1   Aug. 31, 2017

(30) Foreign Application Priority Data

Feb. 29, 2016 (EP) .................................... 16157802

(51) Int. Cl.
*G01N 33/566* (2006.01)
*C07K 14/725* (2006.01)
*C07K 14/705* (2006.01)
*G01N 33/569* (2006.01)

(52) U.S. Cl.
CPC ....... *G01N 33/566* (2013.01); *C07K 14/7051* (2013.01); *C07K 14/70503* (2013.01); *G01N 33/56972* (2013.01); *G01N 2333/70596* (2013.01)

(58) Field of Classification Search
CPC ..................................................... G01N 33/566
USPC ........................................................ 435/7.24
See application file for complete search history.

(56) References Cited

U.S. PATENT DOCUMENTS

| | | | | |
|---|---|---|---|---|
| 5,057,301 A * | 10/1991 | Wilbur | ............... | A61K 51/1093 424/179.1 |
| 8,147,832 B2 * | 4/2012 | Carr | ................... | C07K 16/3076 424/133.1 |
| 8,901,276 B2 * | 12/2014 | Wang | ................. | A61K 49/0039 530/300 |
| 8,902,276 B2 * | 12/2014 | Tsai | .................... | H04L 12/1813 345/156 |
| 2005/0069545 A1 * | 3/2005 | Carr | .................... | C07K 16/2887 424/144.1 |

FOREIGN PATENT DOCUMENTS

WO    WO-9631776 A1 *  10/1996   ....... G01N 33/56966

OTHER PUBLICATIONS

Z. Wang et al. ("Z. Wang", Royal Soc. Chem. Adv. 2014, 7235).*

* cited by examiner

*Primary Examiner* — Sean E Aeder
(74) *Attorney, Agent, or Firm* — Jaquelin K. Spong

(57) ABSTRACT

The invention is directed to a detection reagent for CAR expressing cells according to general formula (1)

$$X_n - S_m - D_o$$

wherein
  X is a polypeptide comprising at least 20 amino acids of which at least two amino acids are connected by at least one disulfide group
  S is a spacer comprising at least 15 carbon atoms
  D is a detection moiety
  m, o are integers independently between 1 and 200
  n is an integer between 4 and 200
with the provisio that X binds to the antigen binding domain of a chimeric antigen receptor of a cell.
The detection agent can be used in a method to detect cells having an antigen binding domain of a chimeric antigen receptor (CAR) binding the detection reagent and preferable to remove the detection moiety D from the detected cell.

6 Claims, 4 Drawing Sheets

Specification includes a Sequence Listing.

SEQUENCE LISTING

```
<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Gly Gly Gly Ser Lys
1               5

<210> SEQ ID NO 2
<211> LENGTH: 25
<212> TYPE: PRT
<213> ORGANISM: homo sapiens

<400> SEQUENCE: 2

Asn Ile Tyr Asn Cys Glu Pro Ala Asn Pro Ser Glu Lys Asn Ser Pro
1               5                   10                  15
```

-continued

```
Ser Thr Gln Tyr Cys Tyr Ser Ile Gln
            20                  25

<210> SEQ ID NO 3
<211> LENGTH: 17
<212> TYPE: PRT
<213> ORGANISM: homo sapiens

<400> SEQUENCE: 3

Cys Glu Pro Ala Asn Pro Ser Glu Lys Asn Ser Pro Ser Thr Gln Tyr
1               5                   10                  15

Cys
```

ASSAY FOR DETECTION OF CHIMERIC ANTIGEN RECEPTOR T CELLS

CROSS REFERENCE TO RELATED APPLICATIONS

This application claims priority to European Application No. 16157802.6 filed Feb. 29, 2016, the content of which is incorporated herein by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention relates to a method and an assay for detection of chimeric antigen receptor carrying cells (CAR).

Chimeric Antigen Receptor (CAR) cells are promising tools in cancer therapy since they can be engineered according to the patient's immune system and type of cancer. For example, EP15196309.7 discloses the reprogramming of hematopoietic stem cells by a viral vector specific for the targeted cancer cells.

An important part of any CAR transduced cell immunotherapy, including its development, pre-clinical research, in-process control and quality control of cell manufacturing, and immunomonitoring of patients, is the detection and isolation of CAR transduced cells and/or the removal of undesired cells before administering of the CAR cells into the patient. Furthermore, determination of the CAR transduction efficiency like frequency and number of transduced cells and the persistence of CAR transduced cells in patients after treatment is of interest. In this respect, it is for example known from De Oliveira et al.: A CD19/Fc fusion protein for detection of anti-CD19 chimeric antigen receptors. Journal of Translational Medicine 2013 11:23 to utilize a CD19 fusion protein for detection of anti-CD19 chimeric antigen receptors. Reagents comprising human IgG1 FC fragment can bind via the FC part to FC receptors (FCR) on expressing cells, e.g. myeloid cells, B cells, or NK cells. This binding lead to false-positive results in flow cytometric analysis. In addition, in in vitro culture the crosslinking of CAR-transduced cells with FCR-expressing immune cells using a CAR-detecting fusion FC protein could induce an effector function by the immune cells, e.g. Antibody-dependent cell-mediated cytotoxicity (ADCC) killing of the CAR-transduced T cells by a cytotoxic NK-cell. Pre-incubation of the cells with serum or antibodies prior to the labeling with FC fusion proteins is required to block FCR binding and reduce these unspecific binding. But addition of FCR blocking reagents is not intended for many applications, especially during in vitro culturing of cells for subsequent therapeutic treatments.

WO2006/074076 A1 discloses an monomerized antibody against CD20 expressing CAR-transduced cells.

Accordingly it was object of the present invention to provide a method which allows labeling of cells without the disadvantage to add FCR blocking reagents.

SUMMARY

The present invention is directed to a detection reagent for CAR expressing cells according to general formula (1)

$$X_n—S_m—D_o \qquad (1)$$

wherein
X is a polypeptide comprising at least 20 amino acids of which at least two amino acids are connected by at least one disulfide group
S is a spacer comprising at least 15 carbon atoms
D is a detection moiety
m, o are integers independently between 1 and 200
n is an integer between 4 and 200
with the provisio that X binds to the antigen binding domain of a chimeric antigen receptor of a cell.

In further embodiments of the invention, the detection reagent according to the invention can be used to bind, isolate, enrich or even activate and expand any cells which express an antigen binding domain of a chimeric antigen receptor on their surface.

Therefore, it is another object of the invention to provide a method for detecting cells expressing an antigen binding domain of a chimeric antigen receptor (CAR), wherein said detection reagent X—S—D is provided to a sample of cells and the cells having an antigen binding domain of a chimeric antigen receptor (CAR) binding the detection reagent are detected via the detection moiety of the detection reagent.

The detection reagent may comprise X, S and D in various ratios to each other. For example, one detection moiety D (o=1) may be conjugated to a plurality of spacers S each bearing one polypetide X (i.e. m=n). In another example, one spacer S (m=1) may be conjugated to a plurality of polypetides X and detection moieties D (n=o). A person skilled in the art will recognize the various possibilities to combine X, S and D.

BRIEF DESCRIPTION OF THE DRAWINGS

Various exemplary details are described with reference to the following figures, wherein.

DETAILED DESCRIPTION

Figure 1:
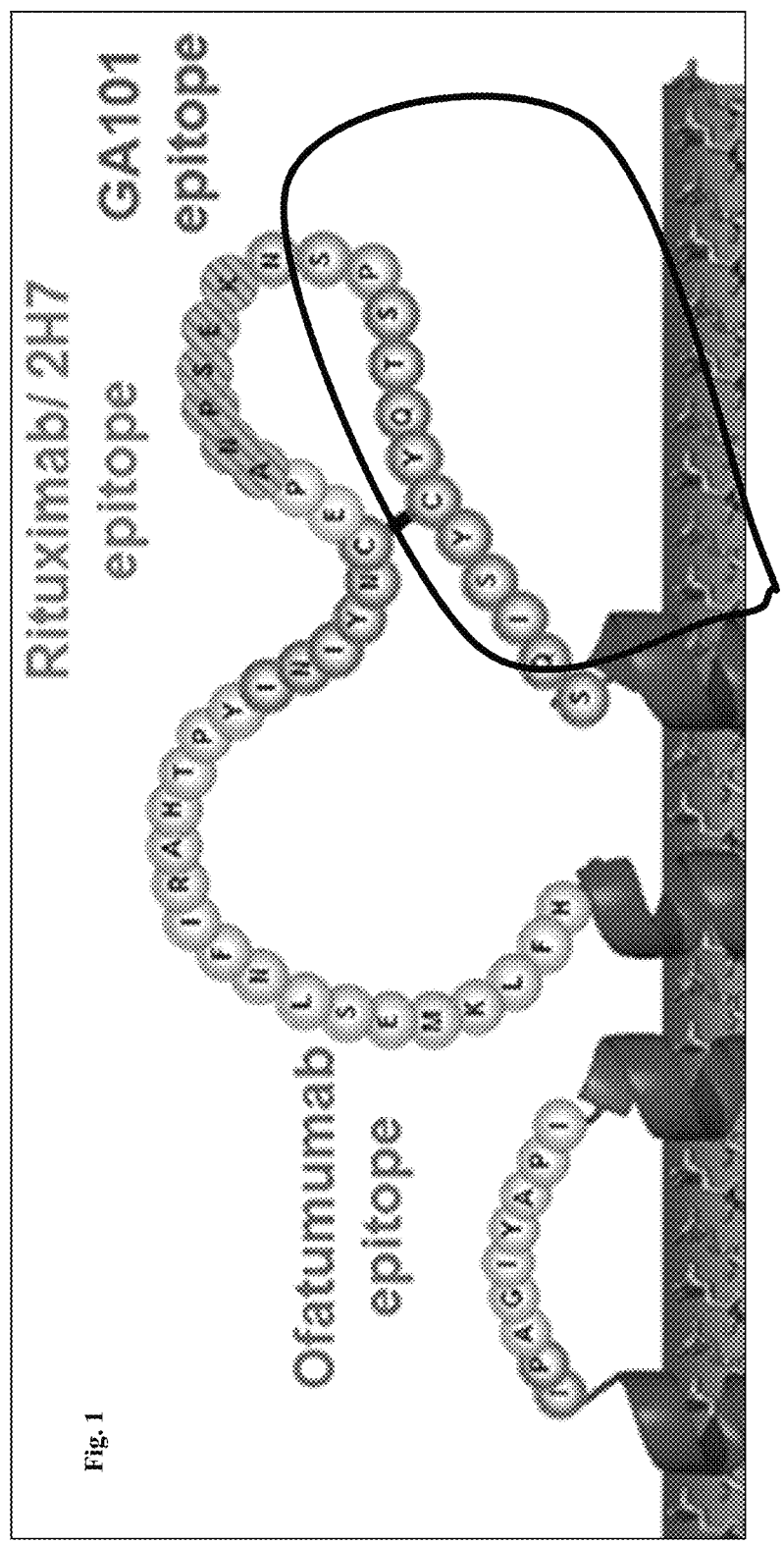
FIG. 1 shows the epitopes of the CD20 target antigen on a CD20 expressing cell

Cells with chimeric antigen receptor (CAR), comprising an extracellular part, at least one intracellular signaling domain, and at least one transmembrane domain are known and for example disclosed in WO2014127261A1, WO2015017214A1, WO2015090229A1, WO2015142661A1 and WO2015150771A1.

The detection reagent of the invention enables the detection, isolation, enrichment or activation of cells expressing a chimeric antigen receptor (CAR). Preferably such cells are T-cells or subsets of T cells, e.g. naive, stem-cell memory, effector memory, central memory or effector T cells, Natural Killer (NK)-cells or NK-cell subsets, or other immune cells.

Definitions

The term "Chimeric antigen receptor" or "CAR" refers to engineered receptors, which are grafted onto cells. In general, a CAR comprises an extracellular domain (extracellular part) comprising the antigen binding domain, a transmembrane domain and an intracellular signaling domain.

The antigen binding domain of the CAR targets specific antigens. The targeting regions may comprise full length heavy chain, Fab fragments, scFvs, divalent single chain antibodies or diabodies, each of which are specific to the target antigen. The antigen binding domain can be derived from the same species or a different species for or in which the CAR will be used in.

The extracellular spacer or hinge region of a CAR is located between its antigen binding domain and transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions of antibodies, accessory proteins, artificial spacer sequences or combinations thereof. Examples of extracellular spacer domains include but are not limited to CD8 alpha hinge.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof.

The term "antigen" refers to a molecular entity that may be soluble or cell membrane bound in particular but not restricted to molecular entities that can be recognized by means of the adaptive immune system including but not restricted to antibodies or TCRs, or engineered molecules including but not restricted to transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The terms "specifically binds" or "specific for" with respect to an antigen-binding domain of an antibody, of a fragment thereof or of a CAR refers to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

Polypeptide X

Polypeptide X comprises at least 20 amino acids of which at least two amino acids are connected by at least one disulfide group. Preferable, polypeptide X is an extracellular sequence of CD20.

For example, polypeptide X may have a sequence of amino acids of CEPANPSEKNSPSTQYC (SEQ ID NO. 1) or NIYNCEPANPSEKNSPSTQYCYSIQ (SEQ ID NO. 2), wherein the amino acids C are connected by a disulfide group.

A person skilled in the art will realize that these sequences can be altered to a certain extend without substantially losing specificity. In variants of the present invention, the disclosed sequences of amino acids may have some amino acids deleted, added or replaced while still retaining the intended function. Therefore, in addition to the disclosed sequence of amino acids, amino acid sequences having a sequence identity of at least 85%, at least 90%, at least 95%, at least 97%, at least 98% or at least 99% at the amino acid sequence as disclosed are within the scope of the present invention.

The detection reagent of the invention may at least 4 and up to 200, preferable between 4 and 50, and more preferable between 4 and 10 polypeptides X (i.e. n is between 4 and 200, 4-50 or 4-10).

Detection Moiety D

The detection moiety D of the detection reagent according to the invention formula (1) may be any moiety possessing a property or function which can be used for direct and indirect detection purposes like those selected from the group consisting of chromophore moiety, fluorescent moiety, phosphorescent moiety, luminescent moiety, light absorbing moiety, radioactive moiety, and chemically detectable moieties like haptens, e.g. biotin, avidin, streptavidin and derivates thereof or magnetic particles.

Preferable, detection moiety D is a fluorochrome, a magnetic particle or biotin.

Suitable fluorescent moieties are those known from the art of immunofluorescence technologies, e.g. flow cytometry or fluorescence microscopy. In these embodiments of the invention, the target cells labeled with the reagent are detected by exciting the detection moiety D and detecting the resulting emission (photoluminescence). In this embodiment, the detection moiety D is preferable a fluorescent moiety.

Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metalloorganic complexes, such as Ru, Eu, Pt complexes.

In a variant of the invention, the detection moiety D, especially a fluorochrome can be destroyed by oxidation in photo- or chemical bleaching procedures (U.S. Pat. No. 7,741,045 B2, EP 0810 428 B1 or DE10143757) such that the fluorescence is quenched.

The magnetic particles used as detection moiety D are preferable nano- to microscale magnetic particle, also known in the art as magnetic bead. The mean diameter of the beads can range from 10 nm to 10 µm. Biocompatible magnetic particles are commercially available and consist of, for example, forms of magnetically iron oxide coated by a shell of dextran molecules or silica. The solid support may also be polymers containing magnetic materials. Suitable particles are commercial available from Miltenyi Biotec GmbH, Germany under the trade name "MicroBeads" and "MACSiBeads".

The detection reagent of the invention may comprise one and up to 200, preferable 1-70, more preferable 4-50 detection moieties D (i.e. o is between 1 and 200, 1-70 or 4-50).

Spacer S

The spacer unit S of the detection reagent comprises at least 15 carbon atoms, and is preferable selected from the group consisting of oligopeptides, polyethylene glycols, enzymatically degradable units or affinity units A, which provide a cleavable, non-covalent connection of detection moiety D and the polypeptide X.

Suitable oligopeptides comprise at least 2 amino acids, preferable up to 10 amino acids. Most preferred are oligopeptides having a sequence of amino acids of GGGSK (SEQ ID NO. 3).

Preferable polyethylene glycols (PEG) comprise 10-200 ethylene glycol units.

As enzymatically degradable spacer S, any molecule which can be cleaved by a specific enzyme can be used. Suitable as enzymatically degradable spacer S are, for example, polysaccharides, proteins, peptides, depsipeptides, polyesters, nucleic acids, and derivatives thereof which can be cleaved by hydrolases. The enzymatically degradable spacer S can be composed of more than one different enzymatically degradable units, which are degradable by the same or different enzyme.

Preferred polysaccharides are, for example, dextrans, pullulans, inulins, amylose, cellulose, hemicelluloses, such as xylan or glucomannan, pectin, chitosan, or chitin.

Detection moiety D and/or polypeptide X can be covalently or non-covalently coupled to the spacer S. Methods for covalently or non-covalently conjugation are known by persons skilled in the art. In case of a covalent bound between the detection moiety D and/or polypeptide X and the spacer S, a direct reaction of an activated group either on the detection moiety D and/or polypeptide X or on the spacer S with an functional group on either the spacer S or on the detection moiety D and/or polypeptide X or via an heterobifunctional linker molecule, which is firstly reacted with one and secondly reacted with the other binding partner is possible.

For a non-covalent or quasi-covalent coupling of detection moiety D to polypeptide X via spacer S, spacer S may be provided with an affinity unit which can be cleaved by a release agent when required. Affinity units comprise for example biotin, avidin and/or streptavidin resulting in a quasi-covalent binding having dissociation constants of less than $10^{-9}$ M.

The term "release agent" refers to any compound capable of binding to a part of the affinity unit. For example, a biotin-avidin affinity unit used as spacer S may be cleaved by streptavidin or adding an access of free biotin. By competitive reaction, the affinity unit is cleaved thereby releasing detection moiety D from polypeptide X (or vice versa). Suitable affinity unit and release agents are disclosed by James Hirsch et al. in Analytical Biochemistry 308 (2002) 343-357.

The affinity unit can be provided with a detection means, i.e. possess a label that can be used for detection. The detection means may be the same or different that those disrobed described for detection moiety D. The use of the affinity unit provided with a detection means as spacer S allows further quantification of the CAR cells.

The detection reagent of the invention may comprise one and up to 200, preferable 1-70, more preferable 4-50 spacers S (i.e. m is between 1 and 200, 1-70 or 4-50).

Cell Detection Methods

A further object of the invention is a method for detecting cells expressing an antigen binding domain of a chimeric antigen receptor (CAR), wherein a detection reagent as disclosed is provided to a sample of cells and the cells having an antigen binding domain of a chimeric antigen receptor (CAR) binding the detection reagent are detected via the detection moiety of the detection reagent.

The cells recognizing the conjugate can be detected by fluorescence emission, by applying a magnetic field or by chemical reaction of the chemically detectable moiety.

The method and the detection reagent of the invention enable detection of target cells labeled with the detection reagent via the detection moiety X.

In one variant of the invention, the detection moiety D is a fluorescent moiety. Target cells labeled with fluorochrome-conjugate are detected by exciting the fluorescent moiety and analyzing the resulting fluorescence signal. The wavelength of the excitation is usually selected according to the absorption maximum of the fluorescent moiety and provided by LASER or LED sources as known in the art. If several different detection moieties are used for multiple color/parameter detection, care should be taken to select fluorescent moieties having not overlapping absorption spectra, at least not overlapping absorption maxima. In case of fluorescent moieties as detection moiety the targets may be detected, e.g., under a fluorescence microscope, in a flow cytometer, a spectrofluorometer, or a fluorescence scanner. Light emitted by chemiluminescence can be detected by similar instrumentation omitting the excitation.

In another variant of the invention, the detection moiety D is a light absorbing moiety, which is detected by the difference between the irradiation light intensity and the transmitted or reflected light intensity. Light absorbing moieties might also be detected by photoacoustic imaging, which uses the absorption of a pulsed laser beam to generate an acoustic like an ultrasonic signal.

Radioactive detection moieties are detected though the radiation emitted by the radioactive isotopes. Suitable instrumentation for detection of radioactive radiation includes, for example, scintillation counters. In case of beta emission electron microscopy can also be used for detection.

Transition metal isotope mass tag moieties are detected by mass spectrometric methods such as ICP-MS, which is integrated in mass cytometry instrumentation.

Use of the Method

The method of the invention can be used for various applications in research, diagnostics and cell therapy.

In a first variant of the invention, biological specimens like cells are detected for counting purposes i.e. to establish the amount or determine the frequency of cells from a sample having a certain set of antigens recognized by the antigen recognizing moieties of the conjugate.

In a second variant, one or more populations of CAR cells are detected from a cell sample and separated as target cells from the non-detected cells. This variant may be used for purification of target cells, for example, in clinical research, diagnostics, and immunotherapy.

Suitable for such separations are especially flow sorters, e.g., FACS or MEMS-based cell sorter systems, for example as disclosed in EP14187215.0 or EP14187214.3, or magnetic separation systems, e.g. MACS.

In a third variant of the method according to the invention, the detection reagent is enzymatically cleaved thereby removing the detection moiety D from the detected cell. In an alternative method, after detection the detection moiety D is subjected to photo- and/or chemical bleaching. Both variants result in unstained cells which may be again provided with detection reagent for cell detection. Such repeated staining and destaining processes can be used to image different parts or cell structures of cells or tissue.

In a further embodiment of the invention, the CAR cells detected by the invention is for use in treatment of cancer in a subject suffering from cancer. Immune cells, e.g. T cells of a subject are isolated. The subject may suffer from said cancer or may be a healthy subject. These cells are genetically modified in vitro to express the CAR of the invention. These engineered cells may be expanded in vitro. In a cellular therapy these engineered cells are infused to a recipient in need thereof. These cells may be a pharmaceutical composition. The infused cells may be able to kill (or at least stop growth of) cancerous cells expressing the antigen, which is recognized by the antigen binding domain of the CAR of the invention in the recipient. The recipient may be the same subject from which the cells were obtained (autologous cell therapy) or may be from another subject of the same species (allogeneic cell therapy).

It is possible to activate and/or expand populations of CAR cells in vitro using the detection reagent by binding to the antigen recognizing moieties of the conjugate, e.g. to access the effector function of the CAR cells. Accordingly, a further object of the invention is a method for activating and expanding cells expressing an antigen binding domain of a chimeric antigen receptor (CAR), wherein a detection reagent as disclosed is provided to a sample of cells and the cells having an antigen binding domain of a chimeric antigen receptor (CAR) binding the detection reagent.

EXAMPLES

Example 1

Multimerization of CD20 Peptide for Flow Cytometric Detection of CD20 CAR-Transduced T Cells FIG. 1 represents a modified version of FIG. 1 of the manuscript from Klein et al. MAbs. 2013 Jan. 1;5(1): 22-33 showing the extracellular part of CD20 and the epitopes of commercially available therapeutic CD20 antibodies. The epitope and the sequence of the polypeptide $CD20_{163-187}$, recognized by CD20 CAR-transduced T cells is highlighted by a black line.

For the following example the $CD20_{163-187}$ polypeptide having C-terminal a spacer of the amino acid GGGSK and at the C-terminus a Biotin was synthetically manufactured by Fmoc chemistry and subsequently a disulfide bound between the cysteine at position 167 and 183 of the $CD20_{163-187}$ polypeptide was introduced to achieve cyclization of the polypeptide which is described by Niederfellner G, Lammens A, Mundigl O, Georges G J, Schaefer W, Schwaiger M, et al. Epitope char-acterization and crystal structure of GA101 provide insights into the molecular basis for type I/II distinction of CD20 antibodies. Blood 2011; 118: 358-67; PMID:21444918; http://dx.doi.org/10.1182/blood- 2010-09-305847 to be required for stabilization of the CD20 protein and therefore for CD20 antibody recognition.

A CAR encoding the antigen-recognizing receptor of the CD20 antibody clone 2H7 (see SEQ ID NO 1 and 2) with an IgG1 extracellular spacer, a CD8 transmembrane and an intracellular signaling domain of 4-1BB-CD3 zeta was generated and cloned into a lentiviral vector (provided by Lentigen Technology, Inc., USA). Human Pan T cells were activated with MACS GMP TransAct kit (Miltenyi Biotec according to the manufacturers recommendations, transduced with the CD20 CAR encoding lentiviral vector or transduced with a control lentiviral vector, not coding for a CAR (Mock-transduced) and expanded in TexMACS medium supplemented with 3% AB serum, 10 ng/mL rec. human IL-7, and 10 ng/mL rec. human IL-15 at 37° C. and 5% CO2 until day 41. The cells were harvested and centrifuged at 300× g for 10 minutes.

Detection of the CD20 CAR target on the CD20 CAR-transduced T cells and for control on Mock-transduced T cells was done for each sample with 1×10E06 T cells in a total volume of 100 μL including P/E/B and the indicated reagents.

For positive control (a) the cells were stained in 100 μL including 1 μL Anti human IgG-Biotin (5 μg/mL) and incubated for 10 minutes at 2-8° C. 1 mL P/E/B was added and the cells were centrifuged at 300× g for 5 minutes at 4° C. The supernatant was aspirated. The cells were resuspended with 70 μL of P/E/B. 10 μL 7-AAD, 10 μL Anti-Biotin-PE, and 10 μgL CD3-FITC were added to the cells. The cells were incubated for 10 minutes at 2-8° C. 1 mL of P/E/B was added and the cells were centrifuged at 300μ g for 5 minutes. The supernatant was aspirated and the cells were resuspended with 500 μL P/E/B.

For the Anti CD20 CAR staining first the CD20-Biotin peptide were mixed with *Streptavidin*-PE (c), Anti-Biotin-PE (e), *Streptavidin*-Vio647 (g), or Anti-Biotin-Fab-Vio647 (i) and incubated for 5 minutes at 2-8° C. (Anti CD20 CAR detection reagent).

Then 10 μL Anti CD20 CAR detection reagent, 10 μL 7-AAD, and 10 μL CD3-FITC were added to the cells and incubated for 10 minutes at 2-8° C. 1 mL of P/E/B was added and the cells were centrifuged at 300× g for 5 minutes. The supernatant was aspirated and the cells were resuspended with 500 μL P/E/B.

For the negative controls the cells were stained in 100 μL including 10 μL 7-AAD, 10 μL CD3-FITC plus 10 μL Anti-Biotin-PE (b, f), *Streptavidin*-PE (d), *Streptavidin*-Vio647 (h), or Anti-Biotin-Fab-Vio647 (j) and incubated for 10 min at 2-8° C. 1 mL of P/E/B was added and the cells were centrifuged at 300× g for 5 minutes. The supernatant was aspirated and the cells were resuspended with 500 μL P/E/B.

The cell acquisition was performed on a MACSQuant Analyzer 10.

Figure 2:
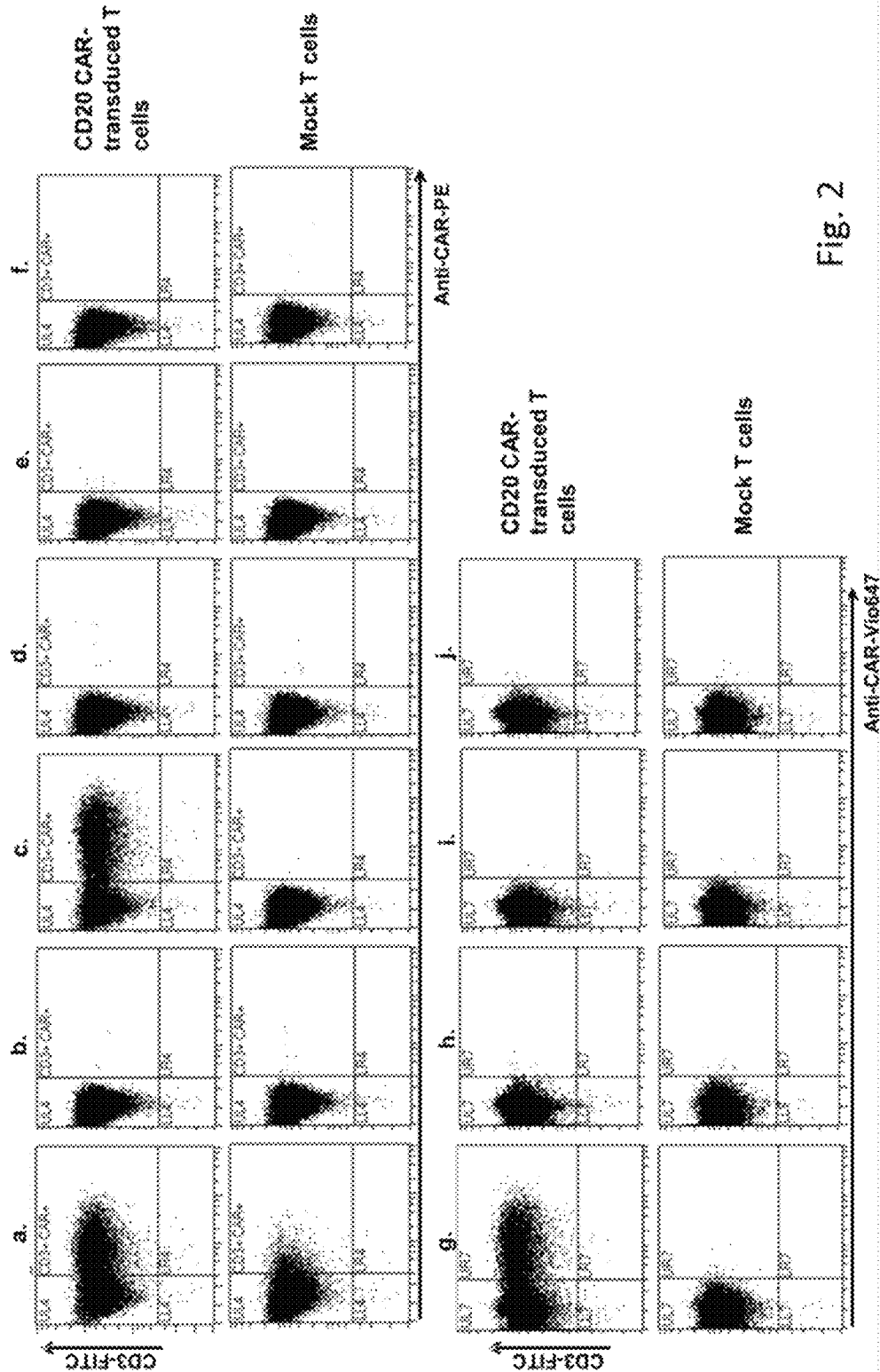
FIG. 2 shows the effect of multimerization of the CD20-Biotin peptide

FIG. 2 shows that multimerization of the CD20-Biotin peptide with *Streptavidin* is having four bindings sites for biotin required for the detection of CD20 CAR on transduced T cells. Binding of the CD20-Biotin peptide to either anti-biotin antibody or Anti-Biotin-Fab is not sufficient to label CD20 CAR on the cells.

Example 2

Multimerized CD20 CAR Detection Reagents Allows Specific Recognizing of CD20 CAR Transduced Cells Cultured in the Presence of Human Serum For this experiment CD20 CAR-transduced or Mock (not CD20 CAR-transduced) T cells were generated as described in Example 1. After 47 days of culture the cells were divided and either cultured in TexMACS GMP grade alone or supplemented with 3% AB serum, 10 ng/mL rec. human IL-7, and 10 ng/mL rec. human IL-15 and cultured with a cell concentration of 2×10E06 cells/mL at 37° C. and 5% $CO_2$ until day 49. On day 49 the cells were harvested and centrifuged at 300× g for 10 minutes. The supernatant was aspirated and the cells were resuspended in P/E/B with a cell concentration of 1×10E08 cells/mL. For each sample 1×10E06 T cells were stained in a total volume of 100 µL including P/E/B and the indicated reagents.

Figure 3:
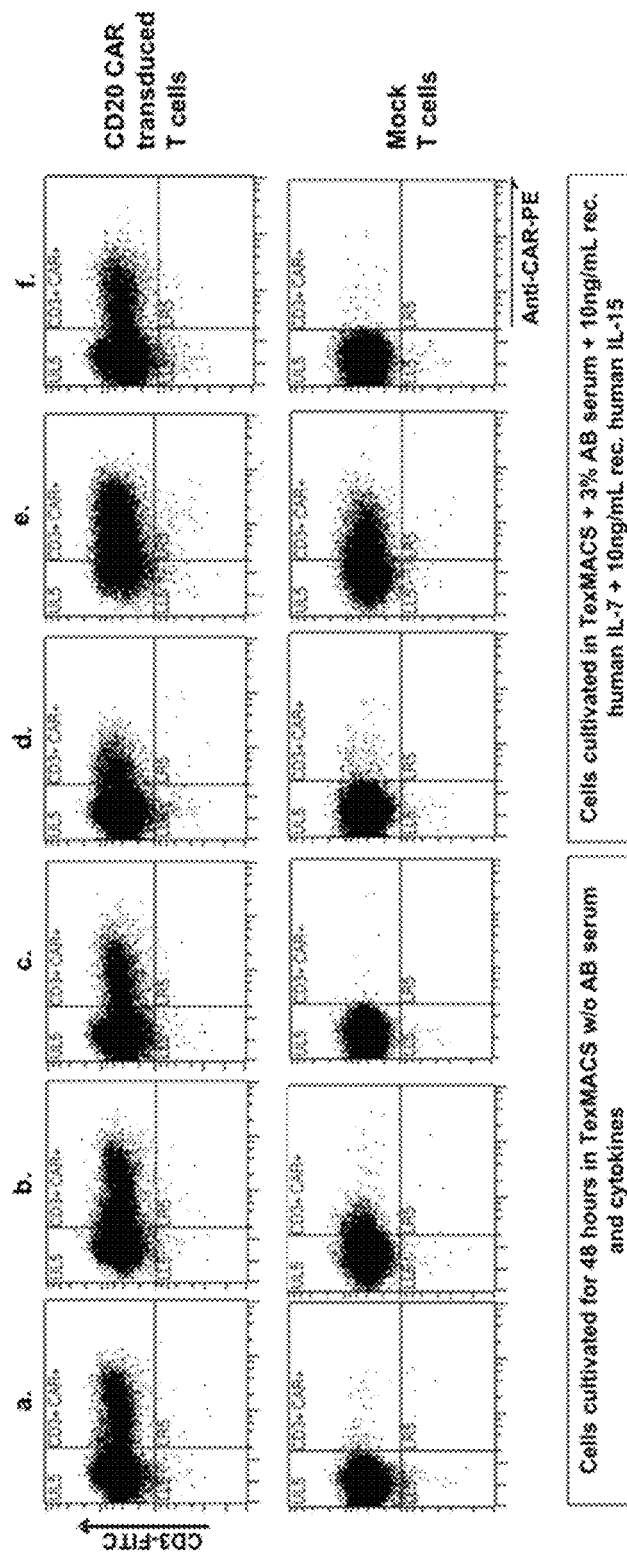
FIG. 3 shows that the effectivity of the method of the invention for labeling of CD20 CAR transduced cells derived from a cell culture containing human serum.

Detection of CD20 CAR transduced cells were performed with Anti human IgG-Biotin/Anti-Biotin-PE staining (FIG. 3a, d) as shown in FIG. 2.

For the protein L staining (b, e) the cells were stained in 100 µL including 1 µL Protein L-Biotin (10 µg/mL) and incubated for 45 minutes at 2-8° C. 1 mL P/E/B was added and the cells were centrifuged at 300× g for 5 minutes at 4° C. The supernatant was aspirated and the cells were resuspended with 1 mL P/E/B. This washing step was performed three times. The cells were resuspended with 70 µL of P/E/B. 10 µL 7-AAD, 10 µL Anti-Biotin-PE, and 10 µL CD3-VioBlue were added to the cells. The cells were incubated for 10 minutes at 2-8° C. 1 mL of P/E/B was added and the cells were centrifuged at 300× g for 5 minutes. The supernatant was aspirated and the cells were resuspended with 500 µL P/E/B.

For the Anti CD20 CAR staining first the CD20-Biotin peptide were mixed with *Streptavidin*-PE (d, f) as shown in FIG. 2. The cell acquisition was performed on a MACSQuant Analyzer 10.

FIG. 2 shows that the effectivity of the method of the invention for labeling of CD20 CAR transduced cells derived from a cell culture containing human serum. This can be observed from the presence of serum during the cultivation of CD20 CAR transduced cells results in unspecific labeling of Mock-transduced cells with Protein L, but not with the CD20 CAR detection reagent.

Example 3

Specificity of the CD20 CAR Detection Reagent

For this experiment CD20 CAR-transduced T cells were used. CD62L+ T cells from a buffy coat were isolated, stimulated with MACS GMP TransAct CD3/CD28, and transduced with the lentiviral vector "MB_TV_LTG020_001" (CD20 CAR) on day 0. The cells were cultured in TexMACS GMP grade supplemented with 3% AB serum, 10 ng/mL rec. human IL-7, and 10 ng/mL rec. human IL-15 at 37° C. and 5% $CO_2$ until day 33. The cells were harvested and centrifuged at 300× g for 10 minutes. The supernatant was aspirated and the cells were resuspended in P/E/B with a cell concentration of 1×10E08 cells/mL.

For each sample 1×10E06 T cells were used and stained in a total volume of 100 µL including P/E/B and the indicated reagents.

First *Streptavidin*-PE were mixed with the CD20-Biotin peptide to form the multimerized CD20 CAR detection reagent. One aliquot of the CD20 CAR detection reagent was incubated with CD20 antibody. For staining control only *Streptavidin*-PE was incubated with CD20 antibody. Incubation was done for 5 minutes at 2-8° C. The cell samples were stained with 10 µL 7-AAD, 10 µL CD3-FITC, and 10 µL SA-PE (a), or 10 µL SA-PE incubated with CD20 antibody (b), or Anti CD20 CAR-PE (c), or 10 µL Anti CD20 CAR-PE incubated with CD20 antibody (d). After 10 minutes incubation at 2-8° C., P/E/B was added for washing and the cells were centrifuged at 300× g for 5 minutes. The supernatant was aspirated and the cells were resuspended with 500 µL P/E/B.

The cell acquisition was performed on a MACSQuant Analyzer 10.

Figure 4:
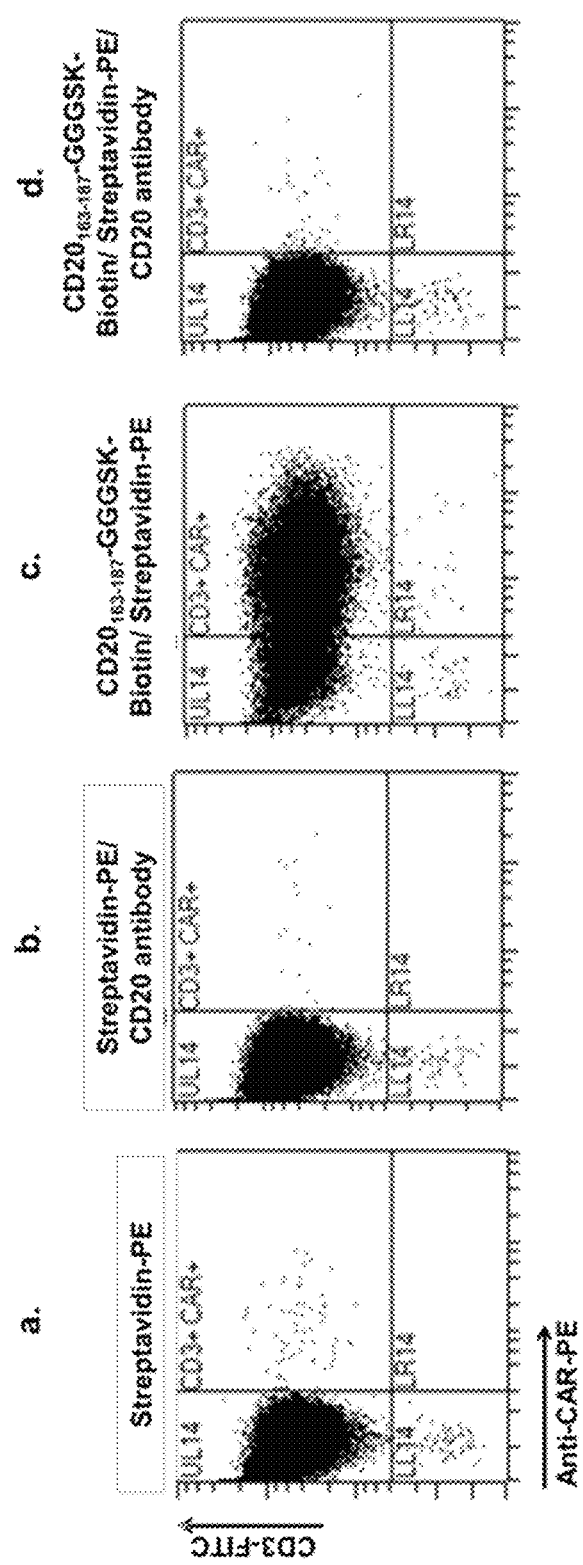
FIG. 4 shows that upon addition of the CD20 antibody to the CD20 CAR detection reagent, the labeling is abrogated, i.e. removed from the cell.

FIG. 4 shows that upon addition of the CD20 antibody to the CD20 CAR detection reagent, the labeling is abrogated, i.e. removed from the cell. This confirms the specificity of the Anti CD20 CAR detection reagent for recognizing the CD20 CAR, which derived from the CD20 antibody clone LT20.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. A method for detecting cells expressing an antigen binding domain of a chimeric antigen receptor (CAR), comprising:

providing a detection reagent according to the general formula (1) to a sample of cells, $X_n—S_m—D_o$ wherein X is a polypeptide comprising at least 20 amino acids of which at least two amino acids are connected by at least one disulfide group having an extracellular sequence of CD20

S is a spacer comprising a polysaccharide having at least 15 carbon atoms selected from the group consisting of dextrans, pullulans, inulins, amylose, cellulose, hemicelluloses, xylan, glucomannan, pectin, chitosan and chitin D is a fluorescent moiety as detection moiety m, o are integers independently between 1 and 200 n is an integer between 4 and 200 with the proviso that X binds to the antigen binding domain of a chimeric antigen receptor of a cell wherein the cells have an antigen binding domain of a chimeric antigen receptor (CAR) binding the detection reagent;

detecting the cells via the detection moiety of the detection reagent; and after detecting the cell via the detection moiety, enzymatically digesting the spacer S thereby removing the detection moiety D from the detected cell.

2. The method according to claim 1 characterized in that the cells recognizing the conjugate are detected by fluorescence emission, applying a magnetic field or by chemical reaction of the chemically detectable moiety.

3. The method according to claim 1 characterized in that the cells detected via the detection moiety D of the detection reagent are separated from the not detected cells.

4. The method according to claim 1 characterized in that after detection, the detection moiety D is subjected to photo- and/or chemical bleaching.

5. The method according to claim 1, characterized in that polypeptide X has a sequence of amino adds of CEPANPSEKNSPSTQYC (SEQ ID NO. 1), wherein the amino adds C are connected by a disulfide group.

6. The method according to claim 1, characterized in that polypeptide X has the sequence of amino adds of NIYN-CEPANPSEKNSPSTQYCYSIQ, (SEQ ID NO. 2), wherein the amino adds Care connected by a disulfide group.

* * * * *